(12) United States Patent
Gupta et al.

(10) Patent No.: US 9,119,967 B2
(45) Date of Patent: Sep. 1, 2015

(54) SYSTEMS AND METHODS FOR REDUCING ELECTROMAGNETIC FIELD-INDUCED HEATING FROM AN IMPLANTABLE PULSE GENERATOR

(71) Applicant: BOSTON SCIENTIFIC NEUROMODULATION CORPORATION, Valencia, CA (US)

(72) Inventors: Gaurav Gupta, Valencia, CA (US); Robert D. Ozawa, Woodland Hills, CA (US); Md Mizanur Rahman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/475,235

(22) Filed: Sep. 2, 2014

(65) Prior Publication Data

US 2015/0073506 A1    Mar. 12, 2015

Related U.S. Application Data

(60) Provisional application No. 61/874,835, filed on Sep. 6, 2013.

(51) Int. Cl.
| | |
|---|---|
| *A61N 1/378* | (2006.01) |
| *A61N 1/36* | (2006.01) |
| *A61N 1/37* | (2006.01) |
| *A61N 1/372* | (2006.01) |

(52) U.S. Cl.
CPC ........ *A61N 1/36142* (2013.01); *A61N 1/36125* (2013.01); *A61N 1/3718* (2013.01); *A61N 1/37223* (2013.01); *A61N 1/3787* (2013.01); *A61N 1/37229* (2013.01)

(58) Field of Classification Search
None
See application file for complete search history.

(56) References Cited

U.S. PATENT DOCUMENTS

| | | |
|---|---|---|
| 5,131,388 A | 7/1992 | Pless et al. |
| 6,181,969 B1 | 1/2001 | Gord |
| 6,240,317 B1 | 5/2001 | Villaseca et al. |

(Continued)

FOREIGN PATENT DOCUMENTS

WO    2010126943    11/2010

OTHER PUBLICATIONS

International Search Report and Written Opinion for PCT/US2014/053732 mailed Dec. 5, 2014.

*Primary Examiner* — Erica Lee
(74) *Attorney, Agent, or Firm* — Lowe Graham Jones PLLC; Bruce E. Black (57) ABSTRACT

An implantable control module for an implantable electrical stimulation system includes a housing with at least a portion of the exterior forming a metallic structure and at least a portion of the interior defining a sealed compartment. The control module further includes an electronic subassembly disposed in the sealed compartment; a connector assembly coupled to the housing and defining a port for receiving a lead; connector contacts disposed in the port to electrically couple with terminals of the lead; feedthrough interconnects extending from the connector assembly into the sealed compartment and coupling the connector contacts to the electronic subassembly; and a coil disposed within or on the housing and configured and arranged to be shorted when an external electromagnetic field is applied in order to resist generation of an eddy current in the metallic structure of the exterior of the sealed housing in response to the external electromagnetic field.

20 Claims, 9 Drawing Sheets

(56) References Cited

U.S. PATENT DOCUMENTS

| | | | |
|---|---|---|---|
| 6,510,345 B1 | 1/2003 | Van Bentem | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,673,999 B1 * | 1/2004 | Wang et al. | 174/36 |
| 6,741,892 B1 | 5/2004 | Meadows et al. | |
| 7,015,393 B2 * | 3/2006 | Weiner et al. | 174/36 |
| 7,244,150 B1 | 7/2007 | Brase et al. | |
| 7,437,193 B2 | 10/2008 | Parramon et al. | |
| 7,620,453 B1 | 11/2009 | Propato et al. | |
| 7,672,734 B2 | 3/2010 | Anderson et al. | |
| 7,761,165 B1 | 7/2010 | He et al. | |
| 7,822,484 B1 | 10/2010 | Zhao et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,364,278 B2 | 1/2013 | Pianca et al. | |
| 2005/0222633 A1 | 10/2005 | Edvardsson | |
| 2007/0150036 A1 | 6/2007 | Anderson | |
| 2008/0039898 A1 | 2/2008 | Lim et al. | |
| 2008/0051854 A1 | 2/2008 | Bulkes et al. | |
| 2009/0149906 A1 | 6/2009 | Ameri et al. | |
| 2011/0112612 A1 | 5/2011 | Rahman | |
| 2011/0137414 A1 | 6/2011 | Litzke et al. | |
| 2011/0234155 A1 * | 9/2011 | Chen et al. | 320/108 |
| 2011/0257703 A1 * | 10/2011 | Kerber et al. | 607/57 |
| 2012/0123500 A1 | 5/2012 | Erickson | |
| 2012/0191167 A1 | 7/2012 | McDonald et al. | |
| 2012/0221074 A1 | 8/2012 | Brase et al. | |
| 2014/0058482 A1 | 2/2014 | Gupta et al. | |

* cited by examiner

SYSTEMS AND METHODS FOR REDUCING ELECTROMAGNETIC FIELD-INDUCED HEATING FROM AN IMPLANTABLE PULSE GENERATOR

CROSS-REFERENCE TO RELATED APPLICATIONS

This application claims the benefit under 35 U.S.C. §119 (e) of U.S. Provisional Patent Application Ser. No. 61/874, 835, filed Sep. 6, 2013, which is incorporated herein by reference.

FIELD

The present invention is directed to the area of implantable electrical stimulation systems and methods of making and using the systems. The present invention is also directed to methods and systems for reducing heating from the implantable pulse generator of systems during exposure of patients to applied electromagnetic fields, as well as methods of making and using the electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead and on a metal case of an implantable pulse generator. These signals can have deleterious effects including, for example, unwanted heating of the tissue causing tissue damage, induced currents in the lead, or premature failure of electronic components.

BRIEF SUMMARY

One embodiment is an implantable control module for an implantable electrical stimulation system and configured and arranged to electrically couple to a lead. The control module includes a housing having an interior and an exterior. At least a portion of the exterior is a metallic structure and at least a portion of the interior defines a sealed compartment. The control module further includes an electronic subassembly disposed in the sealed compartment in the interior of the housing; a connector assembly coupled to the exterior of the housing and defining a port for receiving the lead; connector contacts disposed in the port to electrically couple with terminals of the lead when the lead is operationally received by the port; feedthrough interconnects extending from the connector assembly into the sealed compartment of the interior of the housing and coupling the connector contacts to the electronic subassembly; and a coil disposed within or on the housing and configured and arranged to be shorted when an external electromagnetic field is applied in order to resist generation of an eddy current in the metallic structure of the exterior of the sealed housing in response to the external electromagnetic field.

A further embodiment is a method of operating an electrical stimulation system. The method includes providing the control module describe above implanted in a patient and electrically coupled to an implantable electrical stimulation lead; applying an external electromagnetic field from a magnetic resonance imager to the control module; and resisting generation of an eddy current in the metallic structure of the housing of the control module utilizing the coil, which is shorted, to produce a magnetic flux opposing the external electromagnetic field.

Another embodiment is an implantable control module for an implantable electrical stimulation system to electrically couple to a lead. The control module includes a housing having an interior and an exterior. At least a portion of the exterior is a metallic structure and at least a portion of the interior defines a sealed compartment. The control module further includes an electronic subassembly disposed in the sealed compartment in the interior of the housing; a connector assembly coupled to the exterior of the housing and defining a port for receiving the lead; connector contacts disposed in the port to electrically couple with terminals of the lead when the lead is operationally received by the port; feedthrough interconnects extending from the connector assembly into the sealed compartment of the interior of the housing for electrically coupling the connector contacts to the electronic subassembly; a coil disposed within or on the housing; and a signal generator disposed within the housing and electrically coupled to the coil to generate an opposing flux within the coil in response to an external electromagnetic field to resist generation of an eddy current in the metallic structure of the exterior of the sealed housing.

A further embodiment is a method of operating an electrical stimulation system. The method includes providing the control module described immediately above implanted in a patient and electrically coupled to an implantable electrical stimulation lead; applying an external electromagnetic field from a magnetic resonance imager to the control module; and resisting generation of an eddy current in the metallic structure of the housing of the control module by applying a current from the signal generator to the coil to produce a magnetic flux opposing the external electromagnetic field.

Yet another embodiment is a kit including either of the control modules described above and a lead coupleable to the control module. The lead including a lead body having a distal end, a proximal end, and a longitudinal length, electrodes disposed on the distal end of the lead body, terminals disposed on the proximal end of the lead body for electrically coupling with the connector contact of the control module when the lead is operationally received by the port, and conductors electrically coupling the electrodes to the terminals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to impedance circuitries for modifying impedances of electrical paths of systems during exposure of patients to applied electromagnetic fields, as well as methods of making and using the impedance circuitries and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in for example, U.S. Pat. Nos. 6,181,969; 6,516,227; 6,609,029; 6,609,032; 6,741,892; 7,244,150; 7,672,734; 7,761,165; 7,949,395; and 7,974,706; and U.S. Patent Applications Publication Nos. 2005/0165465, 2007/0150036; 2007/0219595; and 2008/0071320, all of which are incorporated by reference.

Figure 1:
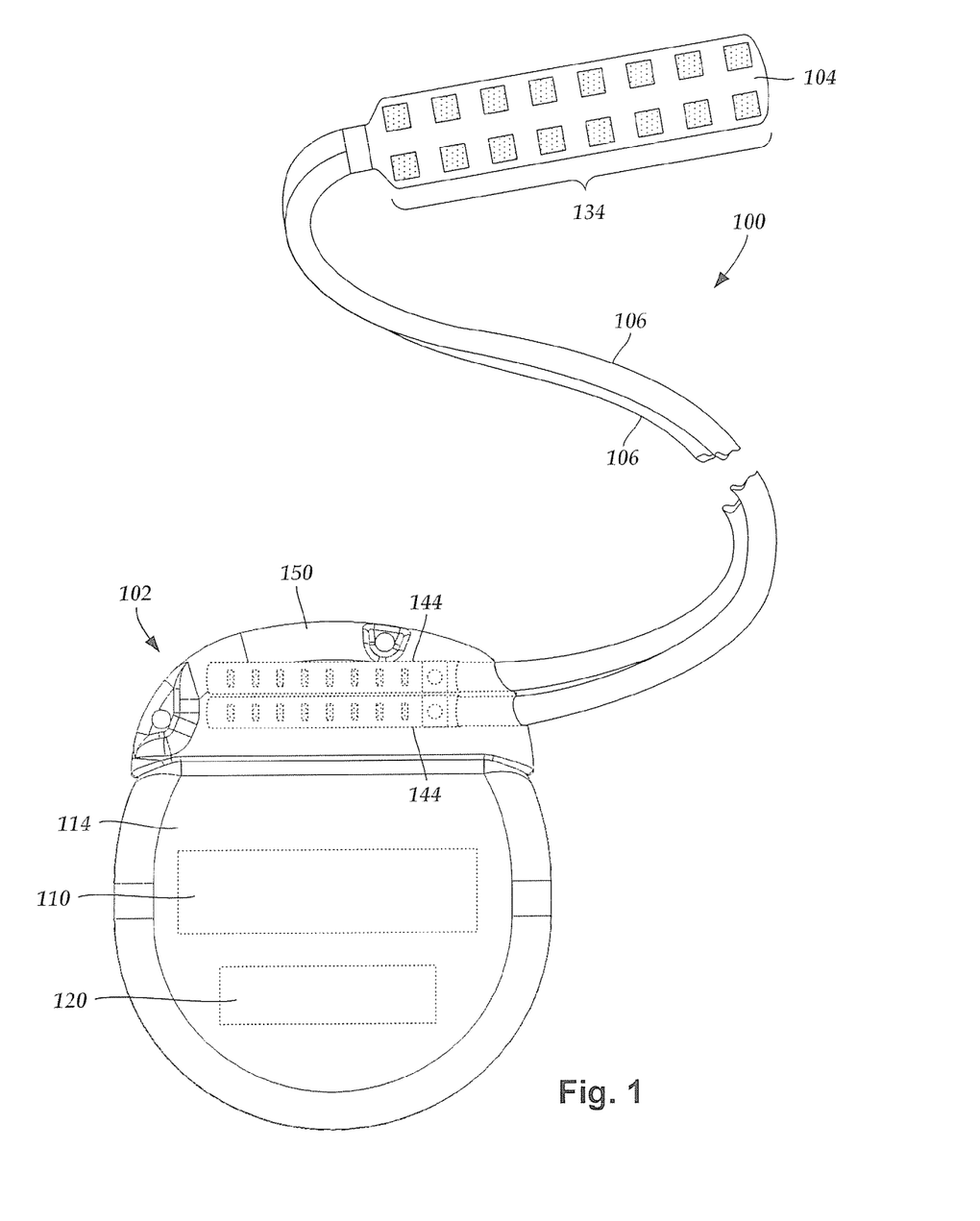
FIG. 1 is a schematic side view of one embodiment of an electrical stimulation system that includes a paddle lead with a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIGS. 3A-3B; and 340 of FIG. 3C) disposed in the connector assembly 144 and terminals (e.g., 310 in FIGS. 3A-3C) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
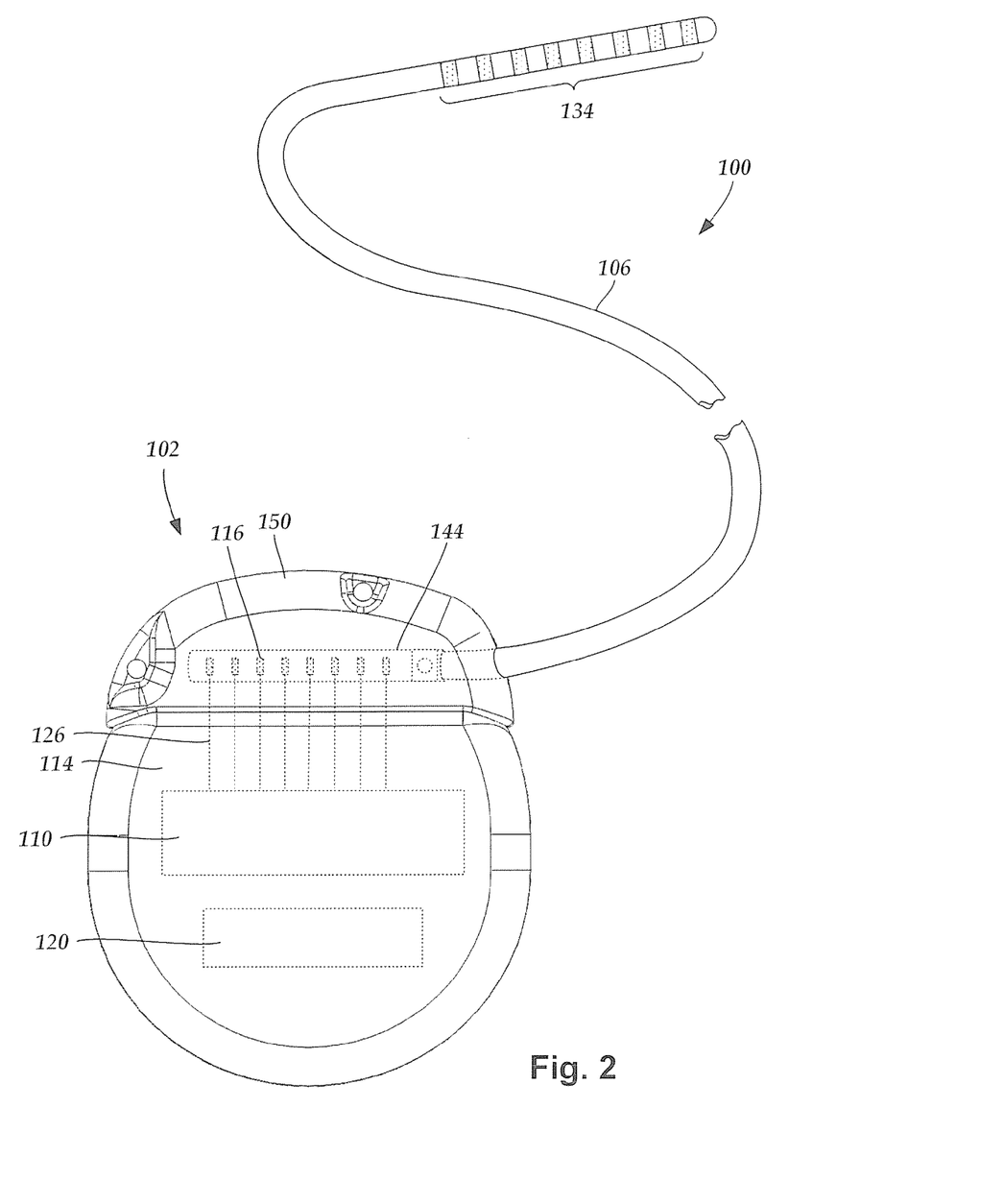
FIG. 2 is a schematic side view of another embodiment of an electrical stimulation system that includes a percutaneous lead coupled to the control module of FIG. 1, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead body 106.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle stimulation, cardiac stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIGS. 3A-3C) are typically disposed at the proximal end of the one or more lead bodies 106 for connection to corresponding conductive contacts (e.g., 316 in FIGS. 3A-3B; and 340 of FIG. 3C) in connector assemblies (e.g., 144 in FIGS. 1-3C) disposed on, for example, the control module 102 (or to other devices, such as conductive contacts on a lead extension, an operating room cable, a splitter, an adaptor, or the like).

Conductive wires (not shown) extend from the terminals (e.g., 310 in FIGS. 3A-3C) to the electrodes 134. Typically, one or more electrodes 134 are electrically coupled to a terminal (e.g., 310 in FIGS. 3A-3C). In some embodiments, each terminal (e.g., 310 in FIGS. 3A-3C) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

A plurality of connector contacts, such as connector contact 116 (see, FIG. 2), are disposed in the connector assembly 144 and are configured and arranged for coupling with terminals (not shown) disposed on a lead when the lead is disposed in the connector assembly 444. In FIG. 2, the connector assembly 144 is shown having eight connector contacts 116. It will be understood that any suitable number of connector contacts 116 may be utilized including, for example, one, two, three, four, five, six, seven, eight, nine, ten, eleven, twelve, fourteen, sixteen, twenty, twenty-four, thirty-two, or more connector contacts 116. The connector contacts 116 are electrically coupled to the electronic subassembly 110 via a plurality of feedthrough interconnects 126 (FIG. 2) that extend into the sealed housing 114.

Figure 3A:
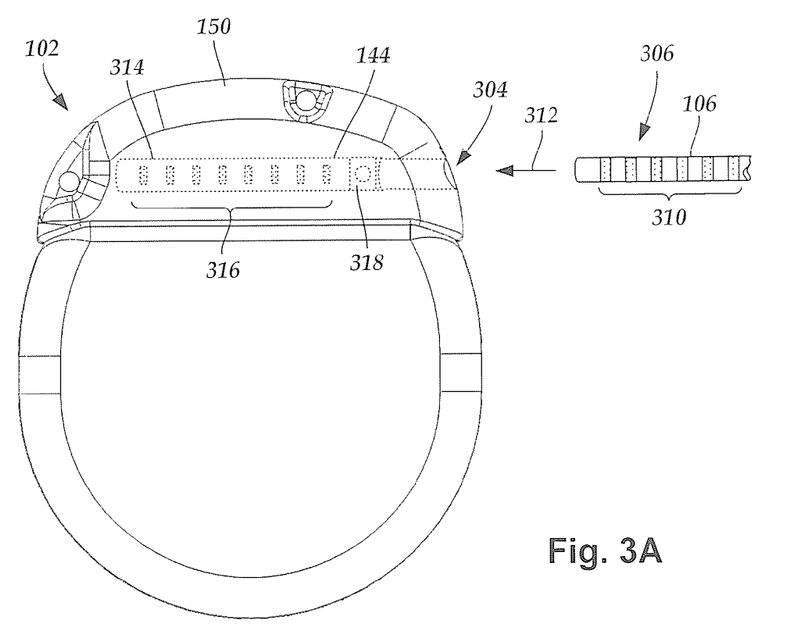
FIG. 3A is a schematic side view of one embodiment of a connector assembly disposed in the control module of FIG. 1, the connector assembly configured and arranged to receive the proximal portion of one of the lead bodies of FIG. 1, according to the invention.
Figure 3B:
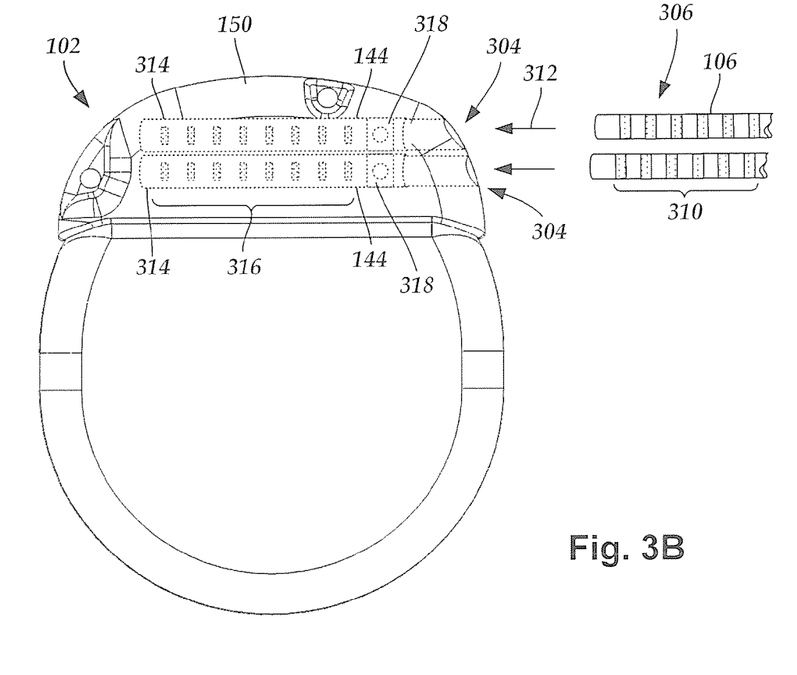
FIG. 3B is a schematic side view of one embodiment of a plurality of connector assemblies disposed in the control module of FIG. 1, the connector assemblies configured and arranged to receive the proximal portions of the lead bodies of FIG. 1, according to the invention.

In at least some embodiments, leads are coupled to connectors disposed on control modules. FIG. 3A is a schematic perspective view of one embodiment of a single connector assembly 144 disposed on the control module 102. FIG. 3B is a schematic perspective view of one embodiment of a plurality of connector assemblies 144 disposed on the control module 102. In at least some embodiments, the control module 102 includes two connector assemblies 144. In at least some embodiments, the control module 102 includes four connector assemblies 144.

In FIGS. 3A and 3B, the proximal ends 306 of one or more lead bodies 106 are shown configured and arranged for insertion to the control module 102. In FIGS. 3A and 3B, the one or more connector assemblies 144 are disposed in the header 150. In at least some embodiments, the header 150 defines one or more ports 304 into which a proximal end 306 of the one or more lead bodies 106 with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 308 to the connector assembly 144 when the lead body 106 is inserted into the connector assembly 144 to prevent undesired detachment of the lead body 106 from the connector assembly 144. For example, the retaining element 318 may include an aperture through which a fastener (e.g., a set screw, pin, or the like) may be inserted and secured against an inserted lead body or lead extension.

When the one or more lead bodies 106 are inserted into the one or more ports 304 the connector contacts 316 can be aligned with the terminals 310 disposed on the one or more lead bodies 106 to electrically couple the control module 102 to the electrodes (134 of FIG. 1) disposed at a distal end of the one or more lead bodies 106. Examples of connector assemblies in control modules are found in, for example, U.S. Pat. No. 7,244,150 and U.S. Patent Application Publication No. 2008/0071320, which are incorporated by reference.

Figure 3C:
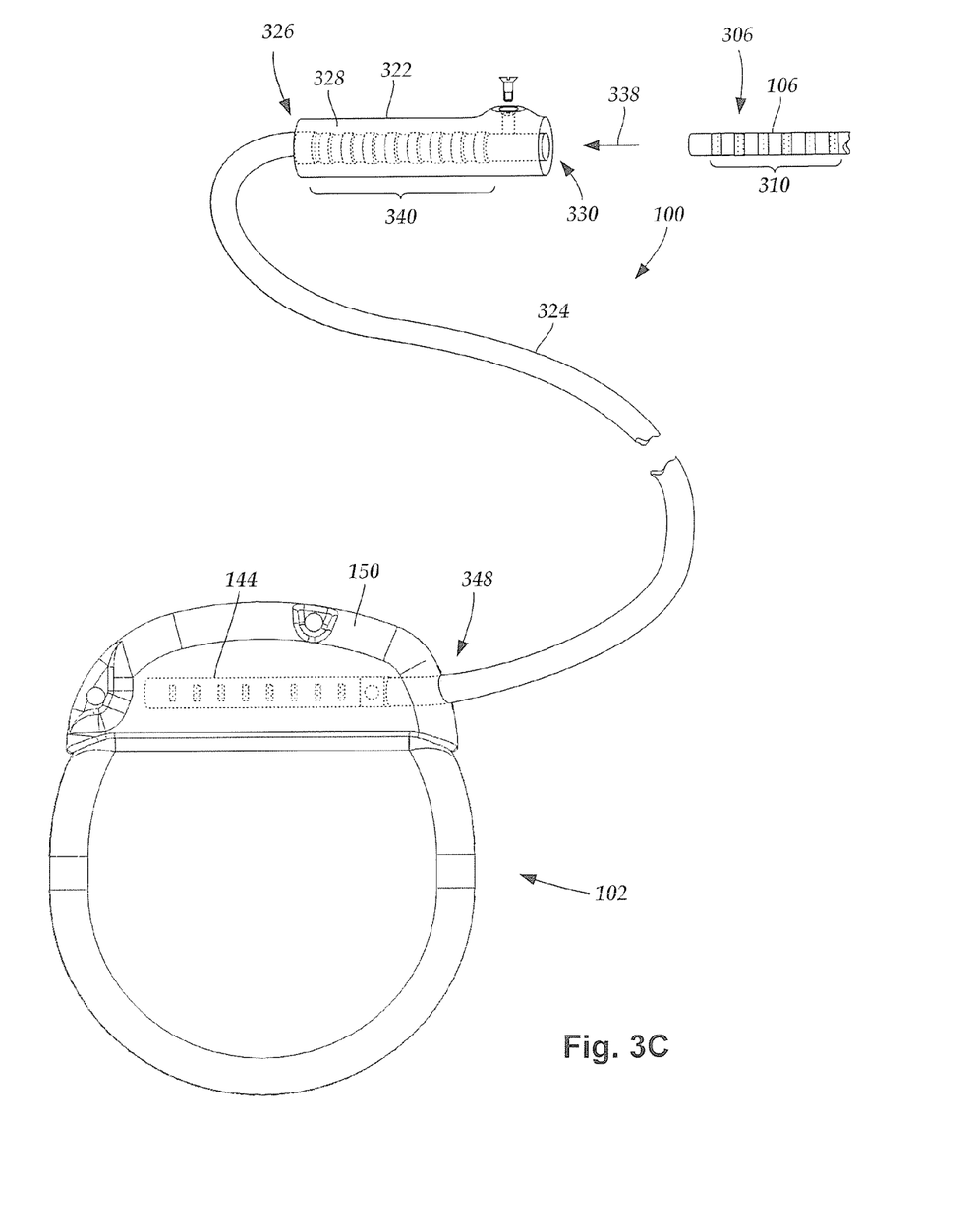
FIG. 3C is a schematic side view of one embodiment of a proximal portion of one of the lead bodies of FIG. 1, a lead extension, and the control module of FIG. 1, the lead extension configured and arranged to couple the lead body to the control module, according to the invention.

In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106 with terminals 310 can be inserted, as shown by directional arrow 338. The lead extension connector assembly 322 also includes a plurality of connector contacts 340. When the lead body 106 is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106.

The proximal end of a lead extension can be similarly configured and arranged as a proximal end of a lead body. The lead extension 324 may include a plurality of conductive wires (not shown) that electrically couple the connector contacts 340 to a proximal end 348 of the lead extension 324 that is opposite to the distal end 326. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102.

Figure 4:
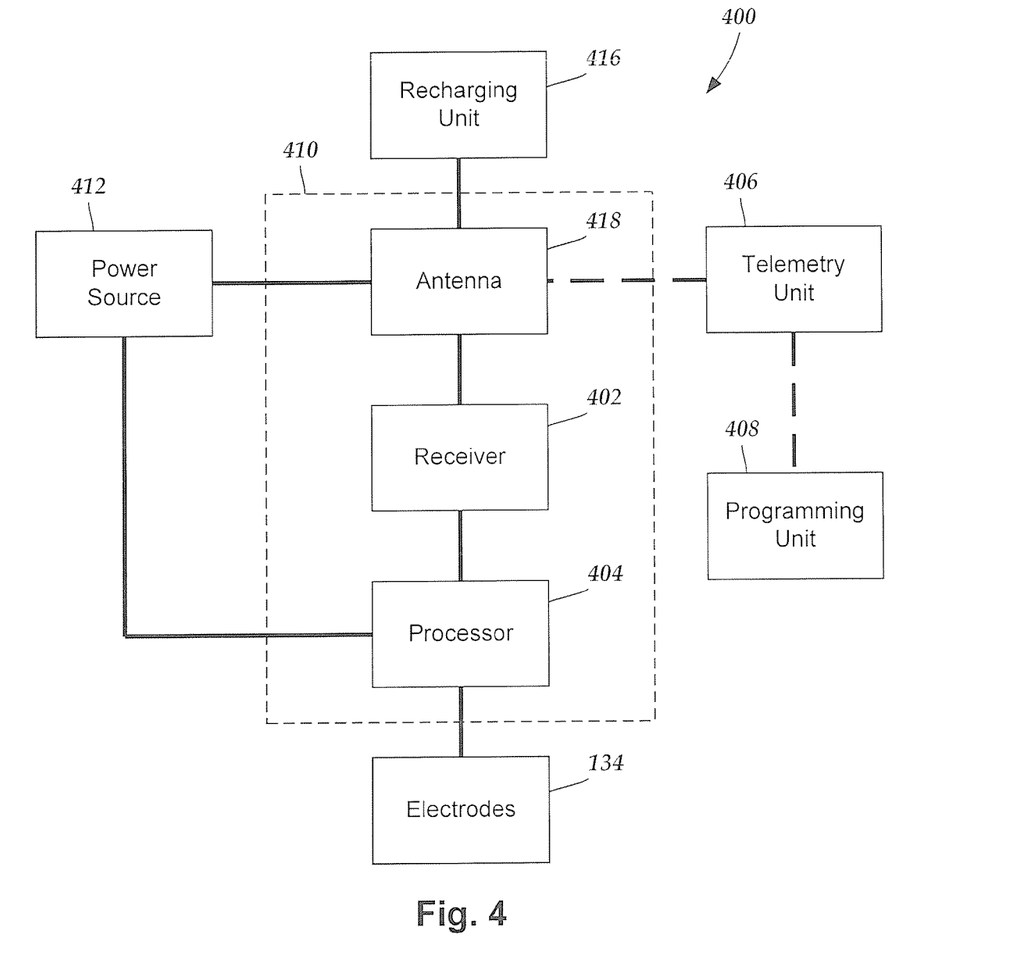
FIG. 4 is a schematic overview of one embodiment of components of a stimulation system, including an electronic subassembly disposed within a control module, according to the invention.

FIG. 4 is a schematic overview of one embodiment of components of an electrical stimulation system 400 including an electronic subassembly 410 disposed within a control module. It will be understood that the electrical stimulation system can include more, fewer, or different components and can have a variety of different configurations including those configurations disclosed in the stimulator references cited herein.

Some of the components (for example, power source 412, antenna 418, receiver 402, and processor 404) of the electrical stimulation system can be positioned on one or more circuit boards or similar carriers within a sealed housing of an implantable pulse generator, if desired. Any power source 412 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 418 or a secondary antenna. The external power source can be in a device that is mounted on the skin of the user or in a unit that is provided near the user on a permanent or periodic basis.

If the power source 412 is a rechargeable battery, the battery may be recharged using the optional antenna 418, if desired. Power can be provided to the battery for recharging by inductively coupling the battery through the antenna to a recharging unit 416 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 404 is generally included to control the timing and electrical characteristics of the electrical stimulation system. For example, the processor 404 can, if desired, control one or more of the timing, frequency, strength, duration, and waveform of the pulses. In addition, the processor 404 can select which electrodes can be used to provide stimulation, if desired. In some embodiments, the processor 404 may select which electrode(s) are cathodes and which electrode(s) are anodes. In some embodiments, the processor 404 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 408 that, for example, allows modification of pulse characteristics. In the illustrated embodiment, the processor 404 is coupled to a receiver 402 which, in turn, is coupled to the optional antenna 418. This allows the processor 404 to receive instructions from an external source to, for example, direct the pulse characteristics and the selection of electrodes, if desired.

In one embodiment, the antenna 418 is capable of receiving signals (e.g., RF signals) from an external telemetry unit 406 which is programmed by a programming unit 408. The programming unit 408 can be external to, or part of, the telemetry unit 406. The telemetry unit 406 can be a device that is worn on the skin of the user or can be carried by the user and can have a form similar to a pager, cellular phone, or remote control, if desired. As another alternative, the telemetry unit 406 may not be worn or carried by the user but may only be available at a home station or at a clinician's office. The programming unit 408 can be any unit that can provide information to the telemetry unit 406 for transmission to the electrical stimulation system 400. The programming unit 408 can be part of the telemetry unit 406 or can provide signals or information to the telemetry unit 406 via a wireless or wired connection. One example of a suitable programming unit is a computer operated by the user or clinician to send signals to the telemetry unit 406.

The signals sent to the processor 404 via the antenna 418 and receiver 402 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 400 to cease operation, to start operation, to start charging the battery, or to stop charging the battery. In other embodiments, the stimulation system does not include an antenna 418 or receiver 402 and the processor 404 operates as programmed.

Optionally, the electrical stimulation system 400 may include a transmitter (not shown) coupled to the processor 404 and the antenna 418 for transmitting signals back to the telemetry unit 406 or another unit capable of receiving the signals. For example, the electrical stimulation system 400 may transmit signals indicating whether the electrical stimulation system 400 is operating properly or not or indicating when the battery needs to be charged or the level of charge remaining in the battery. The processor 404 may also be capable of transmitting information about the pulse characteristics so that a user or clinician can determine or verify the characteristics.

A conventional electrical stimulation system may be potentially unsafe for use with magnetic resonance imaging ("MRI") due to the effects of electromagnetic fields (e.g., radiofrequency fields) in an MRI environment. A common mechanism for causing the electrical interactions between the electrical stimulation system and radiofrequency ("RF") irradiation or magnetic field and magnetic field gradients is common-mode coupling of the applied electromagnetic fields to metal portions of the electrical stimulation system. This can include metal portions of the housing 114 as the housing may be made of metal or include one or more metallic structures, such as electrodes on the housing. Common-mode induced currents can reach amplitudes of greater than one ampere in MRI environments. Such currents can cause heating and potentially disruptive voltages within electronic circuits, such as electronic circuits disposed within the electronic subassembly. The heating of the metallic components of the housing of the control module can cause tissue burning or damage.

The electromagnetic fields, which produce magnetic flux, can, for example, induce eddy currents in the metal housing or other metallic structures of the housing. The eddy currents give rise to resistive heating in the metallic structures of the housing. The heating may damage surrounding tissue. Eddy currents could also cause heating of the battery or other components in the control module which may result in damage to the control module or surrounding tissue.

To address this, one or more coils can be placed in the control module and shorted so that the magnetic flux arising from an external electromagnetic field will induce a current in the coil that will produce an opposing magnetic flux. As an alternative, a signal generator can be attached to the coil to generate the opposing magnetic flux. These arrangements can reduce the total magnetic flux to which the metallic structures of the housing of the control module is subjected and result in smaller eddy currents, or even the absence of eddy currents. The coil may generate some resistive heating, but such heating will generally be less than that which would be generated from the metallic structures of the housing of the control module without the coil, because the coil will typically have lower resistance.

Figure 5:
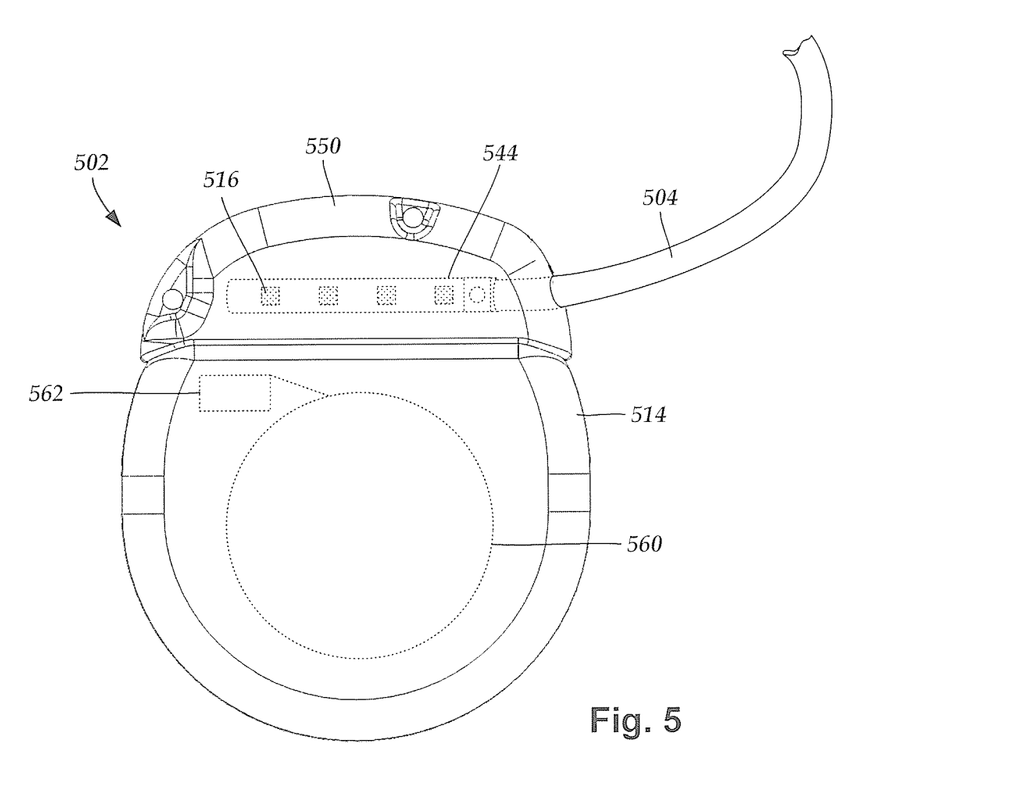
FIG. 5 is a schematic side view of one embodiment of a control module and a lead, the control module including a coil within or on the housing of the control module, according to the invention.

FIG. 5 illustrates one embodiment of a control module 502 and a lead 504. The control module 502 includes a housing 514, header 550, one or more connector assemblies 544 in the header, and one or more connector contacts 516 in the connector assemblies. The control module 502 can also include any of the elements described about with respect to the control modules illustrated in FIGS. 1-4.

The control module 502 also includes a coil 560 that is provided within or on the housing 514. The coil 560 is made of a conductive material, such as a metal or alloy, that is preferably biocompatible. The coil 560 has one or more loops. For example, the coil can have one, two, three, four, five, six, ten, twelve, twenty, fifty, one hundred, or more loops.

The coil 560 can be placed anywhere within or on the housing 514. In some embodiments, the coil 560 is molded into the material that forms the wall of the housing 514. In some embodiments, the coil 560 is disposed in the sealed compartment within the housing. For example, the coil 560 can be attached to the interior surface of the housing 514 or can be attached to a circuit board or other portion of the electronic subassembly 110 (see, FIG. 1). In some embodiments, the coil 560 is placed on the exterior surface of the housing 514.

The coil 560 is placed within or on the housing 514 at a position where an external electromagnetic field (e.g., a RF field or a magnetic field or a magnetic field gradient) can induce a current in the coil. It is believed that the induced current will generate a magnetic flux that opposes the magnetic flux of the electromagnetic field, thereby reducing the or eliminating the total magnetic flux to which the control module is subjected. This can reduce or eliminate eddy currents in the metallic portions of the control module (particularly, those metallic portions on the exterior surface of the housing 514.) It will be understood that a control module can include more than one coil 560. For example, the control module can include one, two, three, four, or more coils 560 to reduce or eliminated eddy currents in the metallic portions of the control module.

In some embodiments, the two ends of the coil 560 are permanently shorted. The ends of the coil 560 are shorted to permit an electromagnetic field to induce current to flow within the coil.

Alternatively, the ends of the coil 560 are shorted only under particular circumstances. Such an arrangement may be useful to, for example, avoid the coil 560 interfering with communications between the control module 502 and an external device. In embodiments in which the coil 560 is disposed on an exterior of the housing 514 or within the material of the housing, leads from the ends of the coil to circuitry within the housing (preferably, using hermetic feedthrough interconnects) may be provided to control shorting or opening of the ends of the coil.

In at least some embodiments, the ends of the coil 560 may be shorted upon initiation by a user or practitioner. For example, the user or practitioner may transmit wirelessly) or otherwise send a command signal to the control module 502 that directs the control module to short the ends of the coil 560. A second signal from the user or practitioner may direct the short circuit to be opened (i.e., unshorted). Alternatively or additionally, the short circuit between ends of the coil 560 may be opened after a predetermined period of time, the duration of which may be user-programmable. This arrangement can be particularly useful for a user that is to have an MRI procedure performed. The user or a practitioner can direct that the coil 560 be shorted during the MRI procedure when the control module will be subjected to RF fields and large magnetic and magnetic gradient fields.

In at least some embodiments, the control module 502 or another device coupled to the control module may include an optional sensor 562 to detect the presence of an external electromagnetic field. If the electromagnetic field exceeds a threshold level, the control module 502 may be directed to short the ends of the coil 560. The threshold level may be permanently set or may be programmable. Again, this arrangement can be particularly useful for a user that is to have an MRI procedure performed. The threshold level can be set so that the RF field or magnetic field associated with the MRI procedure triggers shorting of the ends of the coil 560. Optionally, the sensor 762 may also detect when the external electromagnetic field drops below a threshold level and then direct the short circuit between ends of the coil 560 to be opened.

In some embodiments, the coil 560 may also be used for other tasks. For example, the coil 560 may be used as the antenna 418 of FIG. 4. Thus, the coil could be used for recharging the power source 412 (see, FIG. 4) or to receive signals from, or send signals to, a telemetry unit 406 (see, FIG. 4) or programming unit 408 (see, FIG. 4) or any combination thereof. In at least some embodiments, an optional switch may be provided to automatically, or at user request, switch the coil from use as an antenna to use as a coil to generate an opposing flux.

Figure 6A:
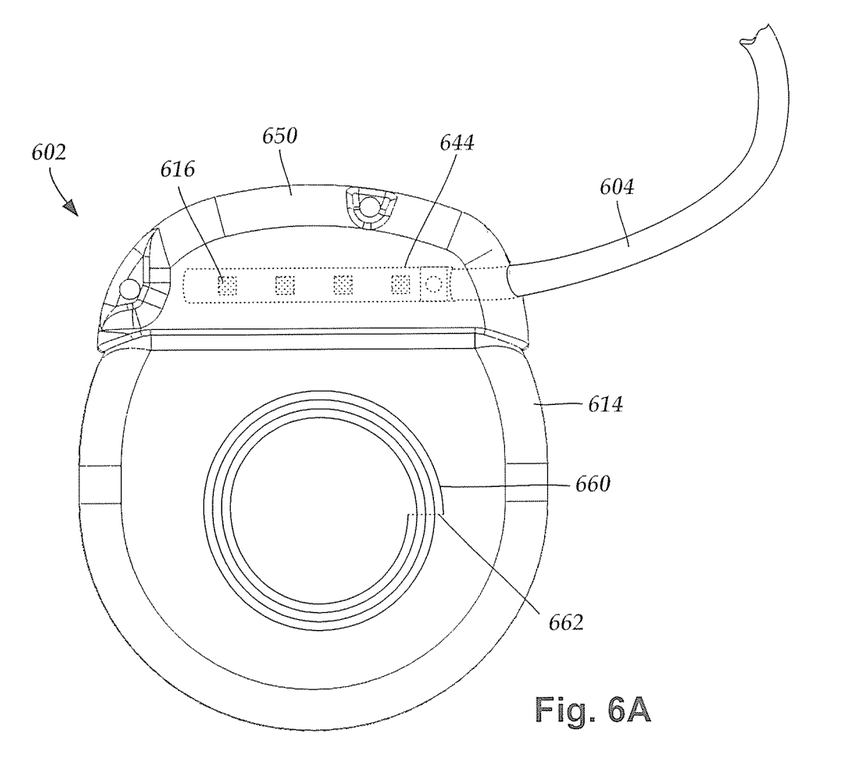
FIG. 6A is a schematic side view of one embodiment of a control module and a lead, the control module including a coil patterned on the housing of the control module, according to the invention.

FIG. 6A illustrates another embodiment of a control module 602 and a lead 604. The control module 602 includes a housing 614, header 650, one or more connector assemblies 644 in the header, and one or more connector contacts 616 in the connector assemblies. The control module 602 can also include any of the elements described about with respect to the control modules illustrated in FIGS. 1-5.

The control module 602 also includes a coil 660 that is patterned onto the housing 614. The coil 660 is made of a conductive material, such as a metal or alloy, that is preferably biocompatible. The coil 660 has one or more loops. For example, the coil can have one, two, three, four, five, six, ten, twelve, twenty, fifty, one hundred, or more loops. The coil 660 can be patterned onto the housing 614 using any suitable technique including, but not limited to, photolithographic or printing methods. The coil 660 can be patterned on the exterior surface of the housing 614 (as illustrated in FIG. 6) or on the interior surface of the housing.

FIG. 6A also illustrates an optional shorting element 662 which electrically couples the ends of the coil 660. This shorting element 662 is insulated from the intermediate loops of the coil. Alternatively, the coil 660 can be permanently or temporarily (i.e., non-permanently) shorted using any of the arrangements and techniques described above with respect to coil 560 of FIG. 5.

Figure 6B:
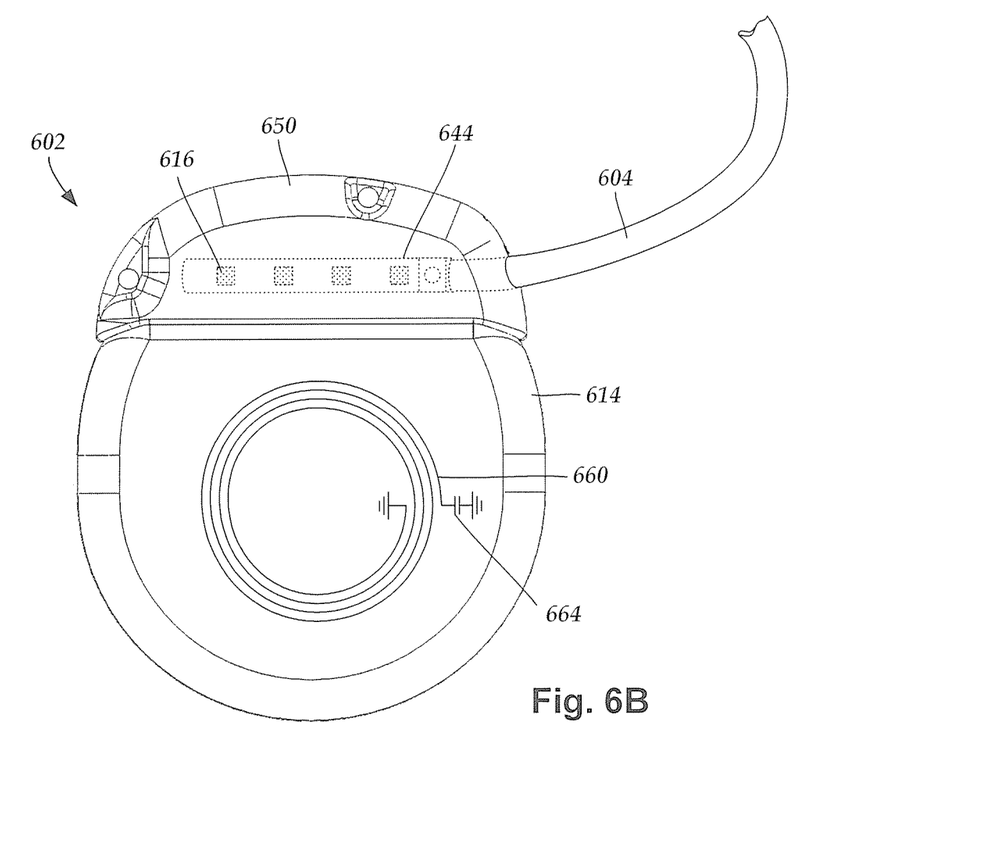
FIG. 6B is a schematic side view of one embodiment of a control module and a lead, the control module including a coil shorted to ground through a tuning capacitor, according to the invention.

FIG. 6B illustrates an alternative embodiment in which the ends of the coil 660 are both shorted to ground with one end shorted through a tuning capacitor 664 (or other tuning circuit). The tuning capacitor can be selected so that the combination of coil and capacitor (e.g., a LC circuit) are tuned to a particular frequency. That frequency can be, for example, any suitable frequency associated with the MRI system or operation. For example, the frequency could be an MRI RF frequency, such as 64 MHz for a 1.5 T MRI magnet or 128 MHz for a 3 T MRI magnet. Alternatively, the frequency could be associated with the MRI gradient field such as a center frequency, or any other frequency, in the range of frequencies associated with the MRI gradient field.

Alternatively, a set of two or more different capacitors can be provided so that the coil arrangement can be tuned to different frequencies. Selection of the appropriate capacitor can be automatic (e.g., using a magnetic field sensor that senses, for example, field frequency or frequency range or strength) or can be initiated by the user who sends a command to the control module to select one of the capacitors, or any combination thereof. It will be understood that the use of one or more tuning capacitors (or other tuning circuitry) can be integrated with any of the coils described herein including those illustrated in FIGS. 5, 6A, and 7.

Figure 7:
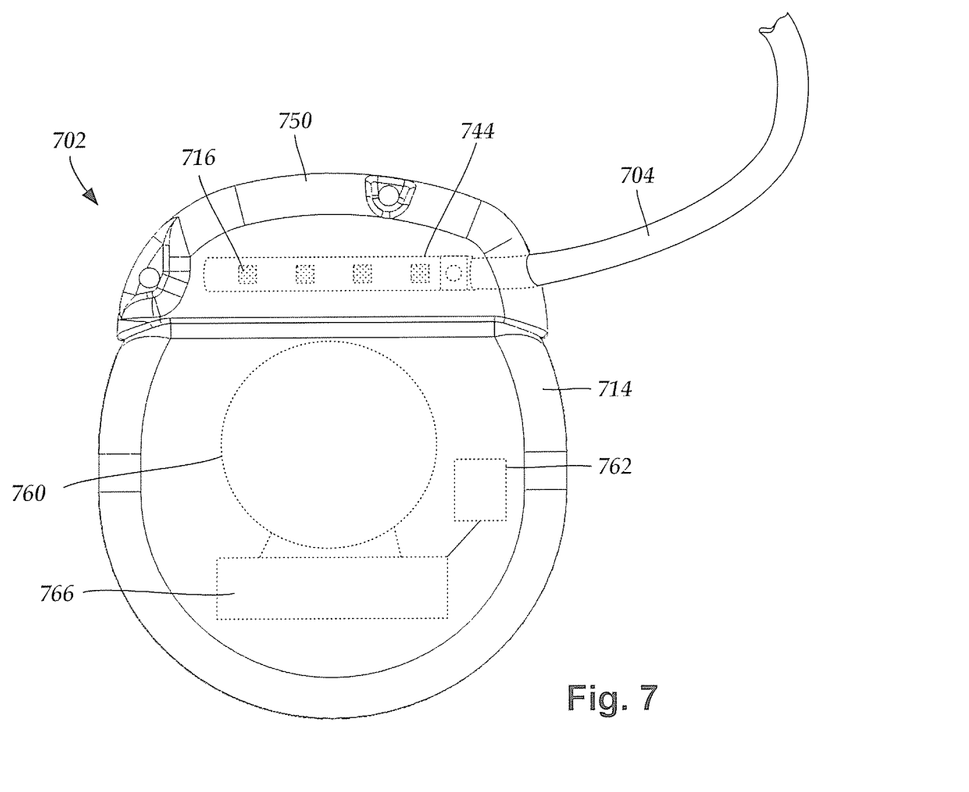
FIG. 7 is a schematic side view of one embodiment of a control module and a lead, the control module including a coil within or on the housing of the control module and an active signal generator coupled to the coil, according to the invention.

Instead of, or in addition to, relying on the induction of current in the coil, a coil can be coupled to an active signal generator to produce the opposing magnetic flux. FIG. 7 illustrates another embodiment of a control module 702 and a lead 704. The control module 702 includes a housing 714, header 750, one or more connector assemblies 744 in the header, and one or more connector contacts 716 in the connector assemblies. The control module 702 can also include any of the elements described about with respect to the control modules illustrated in FIGS. 1-6.

The control module 702 also includes a coil 760 within or on the housing 714. The coil 760 can be any of the coils discussed above with respect to FIGS. 5 and 6. The coil 760 is made of a conductive material, such as a metal or alloy, that is preferably biocompatible. The coil 760 has one or more loops. For example, the coil can have one, two, three, four, five, six, ten, twelve, twenty, fifty, one hundred, or more loops.

The control module 702 also includes an active signal generator 766. The active signal generator provides current to the coil 760 to generate the opposing flux in order to reduce the effects from an external electromagnetic field. In some embodiments, the active signal generator may be directed to generate an opposing flux that cancels all or nearly all (e.g., at least 75%, 80%, 90%, 95%, or 99%) of the incoming flux from the external electromagnetic field. The signal generator 766 may utilize a processor 404 (see, FIG. 4) of the control module 702 or it may have its own processor for directing the generation of the opposing flux in the coil 760.

In at least some embodiments, the signal generator 766 can be activated upon initiation by a user or practitioner. For example, the user or practitioner may transmit or otherwise send a signal to the control module 702 that directs that the signal generator to provide a current to the coil 760. A second signal from the user or practitioner may deactivate the signal generator. Alternatively or additionally, the signal generator may be activated for only a predetermined period of time, the duration of which may be user-programmable. This arrangement can be particularly useful for a user that is to have an MRI procedure performed. The user or a practitioner can direct that the activation of the signal generator 766 during the MRI procedure when the control module will be subjected to RF fields and large magnetic and magnetic gradient fields.

In at least some embodiments, the control module 702 or another device coupled to the control module may include an optional sensor 762 to detect the presence of an external electromagnetic field. In some embodiments, the sensor 762 can detect a magnitude or phase (or both magnitude and phase) of the electromagnetic field or the flux generated by the electromagnetic field. If the electromagnetic field exceeds a threshold level, the signal generator 766 may be activated to send current through the coil 560 to generate the opposing flux. The threshold level may be permanently set or may be programmable. Again, this arrangement can be particularly useful for a user that is to have an MRI procedure performed. The threshold level can be set so that the RF field or magnetic field associated with the MRI procedure triggers the signal generator 766. Optionally, the sensor 762 may also detect when the external electromagnetic field drops below a threshold level and then direct the signal generator 766 to be deactivated.

In some embodiments, the coil 760 may also be used for other tasks. For example, the coil 760 may be used as the antenna 418 of FIG. 4. Thus, the coil could be used for recharging the power source 412 (see, FIG. 4) or to receive signals from, or send signals to, a telemetry unit 406 (see, FIG. 4) or programming unit 408 (see. FIG. 4) or any combination thereof. In at least some embodiments, an optional switch may be provided to automatically, or at user request, switch the coil from use as an antenna to use as a coil to generate an opposing flux.

The above specification, examples and data provide a description of the manufacture and use of the composition of the invention. Since many embodiments of the invention can be made without departing from the spirit and scope of the invention, the invention also resides in the claims hereinafter appended.

The invention claimed is:

1. An implantable control module for an implantable electrical stimulation system and configured and arranged to electrically couple to a lead, the control module comprising:

a housing having an interior and an exterior, wherein at least a portion of the exterior is a metallic structure and at least a portion of the interior defines a sealed compartment;

an electronic subassembly disposed in the sealed compartment in the interior of the housing;

a connector assembly coupled to the exterior of the housing, the connector assembly defining a port configured and arranged for receiving the lead;

a plurality of connector contacts disposed in the port, the connector contacts configured and arranged to electrically couple with terminals of the lead when the lead is operationally received by the port;

a plurality of feedthrough interconnects extending from the connector assembly into the sealed compartment of the interior of the housing, the plurality of feedthrough interconnects electrically coupling the plurality of connector contacts to the electronic subassembly; and a coil disposed within or on the housing and configured and arranged to be shorted when an external electromagnetic field is applied in order to resist generation of an eddy current in the metallic structure of the exterior of the sealed housing in response to the external electromagnetic field.

2. The control module of claim 1, wherein the coil is permanently shorted.

3. The control module of claim 1, wherein the coil is configured and arranged to become shorted upon application of an external electromagnetic field exceeding a threshold field strength.

4. The control module of claim 3, further comprising a sensor operatively coupled to the coil and configured and arranged to sense a presence of an electromagnetic field.

5. The control module of claim 1, wherein the coil is configured and arranged to become shorted in response to user initiation.

6. The control module of claim 5, wherein the coil is configured and arranged to become shorted in response to user initiation using a wireless command signal.

7. The control module of claim 1, wherein the coil is disposed within the sealed compartment.

8. The control module of claim 1, wherein the housing has at least one housing wall and the coil is disposed within the at least one housing wall.

9. The control module of claim 1, wherein the coil is disposed on an exterior of the housing.

10. The control module of claim 1, wherein the coil is also configured and arranged for reception of signals from an external device and the coil is coupled to the electronic subassembly to provide the signals from the external device to the electronic subassembly.

11. The control module of claim 1, further comprising a power source, wherein the coil is also configured and arranged for reception of signals from an external device and delivering those signals to the power source to charge the power source.

12. The control module of claim 1, wherein the coils has two ends that are shorted to ground with one of the two ends shorted through a tuning capacitor.

13. A system for electrical stimulation, the system comprising
the control module of claim 1; and
a lead electrically coupleable to the control module, the lead comprising
a lead body having a distal end, a proximal end, and a longitudinal length,
a plurality of electrodes disposed on the distal end of the lead body,
a plurality of terminals disposed on the proximal end of the lead body and configured and arranged for electrically coupling with the connector contacts of the control module when the lead is operationally received by the port, and
a plurality of conductors electrically coupling the plurality of electrodes to the terminals.

14. A method of operating an electrical stimulation system, the method comprising:
providing the control module of claim 1 implanted in a patient and electrically coupled to an implantable electrical stimulation lead;
applying an external electromagnetic field from a magnetic resonance imager to the control module; and
resisting generation of an eddy current in the metallic structure of the housing of the control module utilizing the coil, which is shorted, to produce a magnetic flux opposing the external electromagnetic field.

15. The method of claim 14, further comprising, after applying the external electromagnetic field and prior to resisting generation of an eddy current, shorting the coil.

16. The method of claim 14, further comprising, after applying the external electromagnetic field and prior to resisting generation of an eddy current, sensing the electromagnetic field using a sensor coupled to the control module.

17. An implantable control module for an implantable electrical stimulation system and configured and arranged to electrically couple to a lead, the control module comprising:
a housing having an interior and an exterior, wherein at least a portion of the exterior is a metallic structure and at least a portion of the interior defines a sealed compartment;
an electronic subassembly disposed in the sealed compartment in the interior of the housing;
a connector assembly coupled to the exterior of the housing, the connector assembly defining a port configured and arranged for receiving the lead;
a plurality of connector contacts disposed in the port, the connector contacts configured and arranged to electrically couple with terminals of the lead when the lead is operationally received by the port;
a plurality of feedthrough interconnects extending from the connector assembly into the sealed compartment of the interior of the housing, the plurality of feedthrough interconnects electrically coupling the plurality of connector contacts to the electronic subassembly;
a coil disposed within or on the housing; and
a signal generator disposed within the housing and electrically coupled to the coil and configured and arranged to generate an opposing flux within the coil in response to an external electromagnetic field to resist generation of an eddy current in the metallic structure of the exterior of the sealed housing.

18. The control module of claim 17, further comprising a sensor operatively coupled to the signal generator and configured and arranged to sense a presence of an electromagnetic field.

19. The control module of claim 18, wherein the sensor is configured and arranged to determine a phase and an amplitude of the electromagnetic field.

20. A method of operating an electrical stimulation system, the method comprising:
providing the control module of claim 17 implanted in a patient and electrically coupled to an implantable electrical stimulation lead;
applying an external electromagnetic field from a magnetic resonance imager to the control module; and
resisting generation of an eddy current in the metallic structure of the housing of the control module by applying a current from the signal generator to the coil to produce a magnetic flux opposing the external electromagnetic field.

* * * * *